United States Patent
Brilliant et al.

(10) Patent No.: US 9,387,058 B2
(45) Date of Patent: *Jul. 12, 2016

(54) HOLDER FOR A CONCEALED TOOTH CLEANING IMPLEMENT

(71) Applicants: Margo Brilliant, Miami, FL (US); Jo Anne Brilliant, Annapolis, MD (US)

(72) Inventors: Margo Brilliant, Miami, FL (US); Jo Anne Brilliant, Annapolis, MD (US)

(73) Assignee: G And E International LLC

(*) Notice: Subject to any disclaimer, the term of this patent is extended or adjusted under 35 U.S.C. 154(b) by 46 days.

This patent is subject to a terminal disclaimer.

(21) Appl. No.: 14/621,834

(22) Filed: Feb. 13, 2015

(65) Prior Publication Data

US 2015/0164623 A1    Jun. 18, 2015

Related U.S. Application Data

(63) Continuation of application No. 13/551,901, filed on Jul. 18, 2012, now Pat. No. 8,973,590.

(60) Provisional application No. 61/508,748, filed on Jul. 18, 2011.

(51) Int. Cl.
  *A61C 15/02*    (2006.01)
  *A61C 3/02*    (2006.01)
  *A45D 40/00*    (2006.01)

(52) U.S. Cl.
  CPC . *A61C 15/02* (2013.01); *A61C 3/02* (2013.01); *A45D 40/00* (2013.01)

(58) Field of Classification Search
  CPC ........... A61C 15/02; A61C 3/02; A45D 40/00
  USPC ......... 132/321–329, 309; 206/63.5, 349, 368, 206/380, 457
  See application file for complete search history.

(56) References Cited

U.S. PATENT DOCUMENTS

| | | | | | |
|---|---|---|---|---|---|
| 2,859,754 | A | * | 11/1958 | Futterer | 132/145 |
| 3,802,445 | A | * | 4/1974 | Wesley | 132/321 |
| 4,033,007 | A | * | 7/1977 | Hadary | 132/328 |
| 4,326,548 | A | * | 4/1982 | Wagner | 132/328 |
| 4,342,324 | A | * | 8/1982 | Sanderson | 132/324 |
| 4,509,541 | A | * | 4/1985 | Manciocchi, Jr. | 132/322 |
| 4,800,905 | A | * | 1/1989 | Stuart | 132/328 |
| 6,082,999 | A | * | 7/2000 | Tcherny et al. | 132/321 |
| 6,234,182 | B1 | * | 5/2001 | Berglund | 132/323 |
| 6,247,477 | B1 | * | 6/2001 | Wagner | 132/309 |
| 6,418,940 | B1 | * | 7/2002 | Tcherny et al. | 132/321 |
| 2004/0094180 | A1 | * | 5/2004 | Hsu | 132/321 |
| 2009/0078280 | A1 | * | 3/2009 | Fishman | 132/328 |

* cited by examiner

*Primary Examiner* — Luan K Bui
(74) *Attorney, Agent, or Firm* — Robert M. Schwartz

(57) ABSTRACT

The present invention is a disguised holder or case that appears to be a lipstick application dispenser but has there within a dental scaler concealed in a faux lipstick tube. The device is designed to fool an observer into believing that the user is applying lipstick rather than picking at or removing food between teeth and therefore can be used by a person in public places.

2 Claims, 4 Drawing Sheets

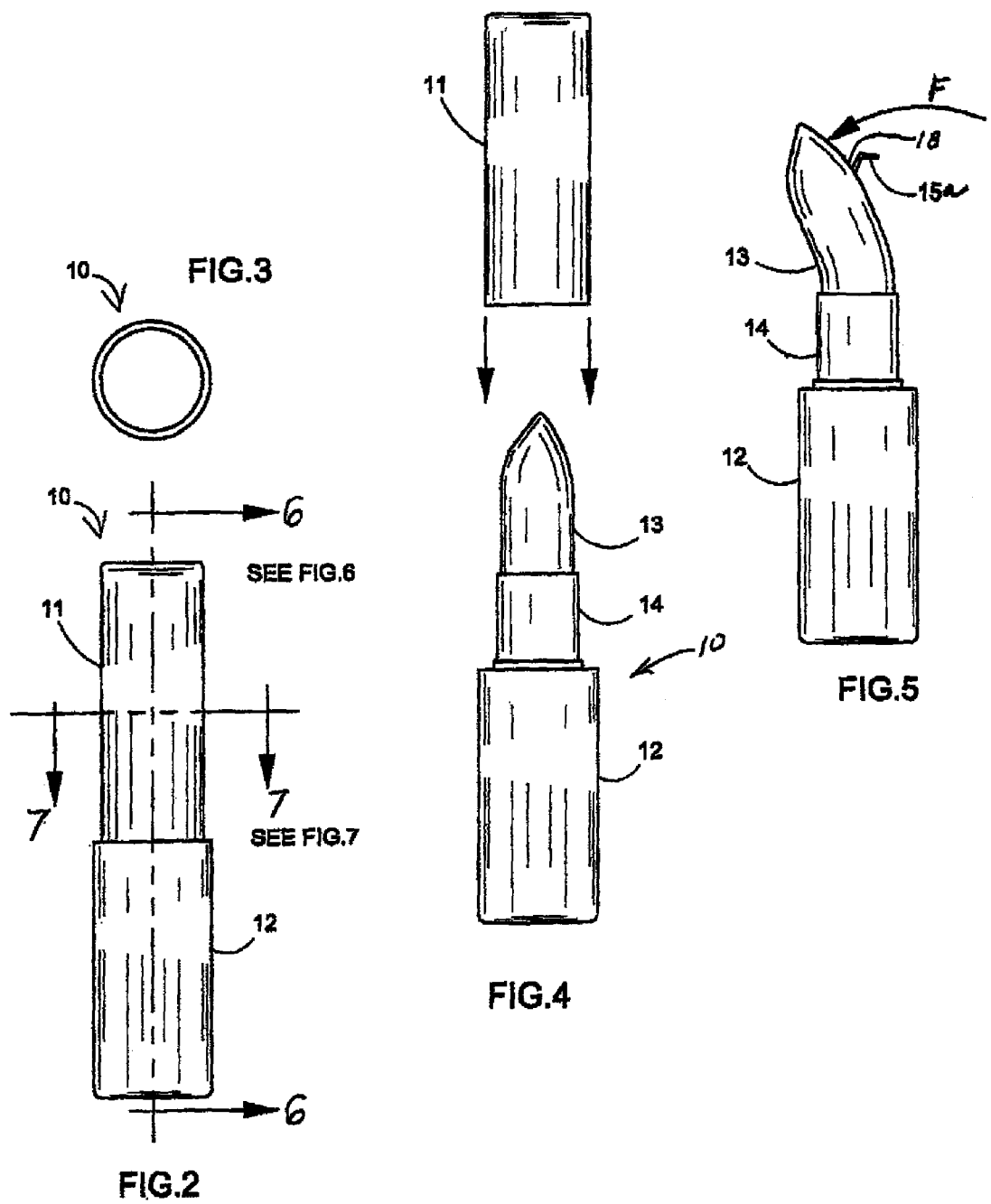

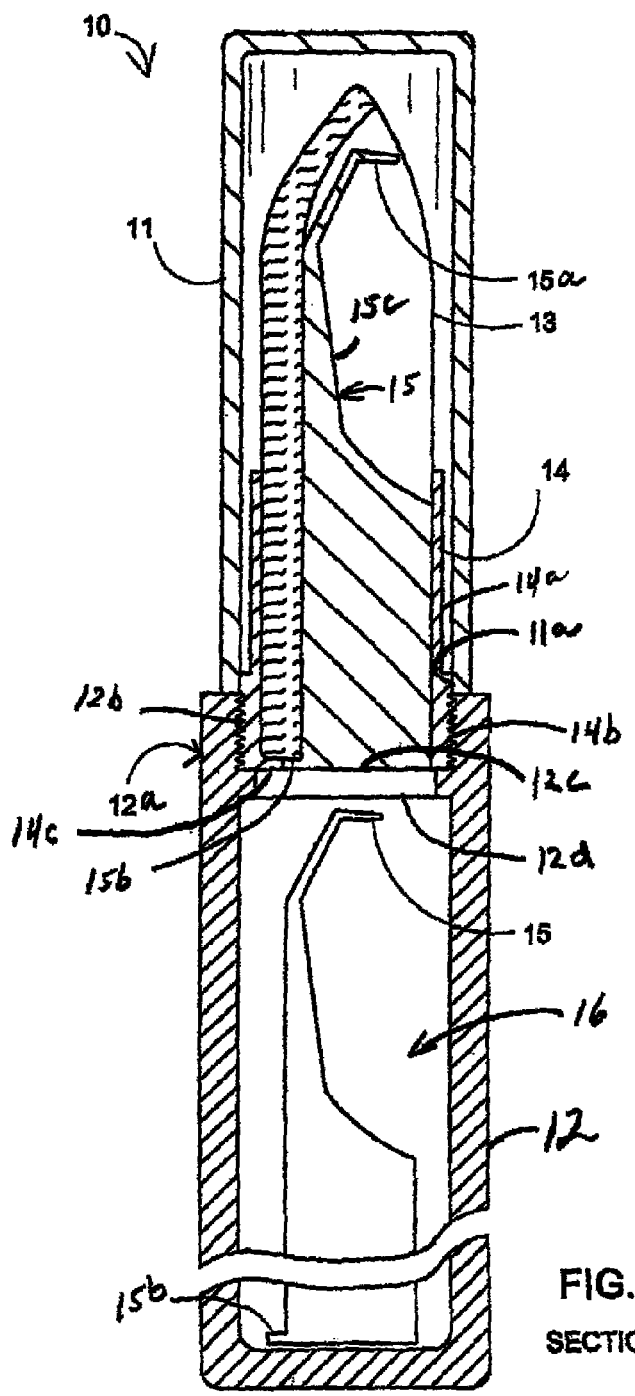
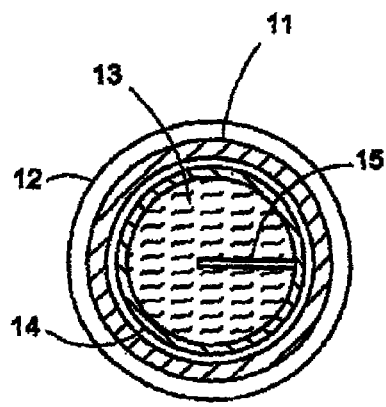
FIG.7
SECTION 7-7 OF FIG.2
FIG.6
SECTION 6-6 OF FIG.2

US 9,387,058 B2

HOLDER FOR A CONCEALED TOOTH CLEANING IMPLEMENT

CROSS REFERENCE TO RELATED APPLICATIONS

This application is a continuation application of U.S. patent application Ser. No. 13/551,901, filed, Jul. 18, 2012, now issued U.S. Pat. No. 8,973,590, entitled Holder for Concealed Tooth Cleaning Implement, which claims the benefit of U.S. Provisional Application Ser. No. 61/508,748, filed on Jul. 18, 2011, entitled "Concealed Scalar," the prior applications are herewith incorporated by reference in their entirety.

BACKGROUND OF THE INVENTION

The field of the present invention relates to dental implements for cleaning food and debris from a person's teeth using a toothpick or dental scaler or similar device.

BRIEF SUMMARY OF THE INVENTION

The present invention is a holder for a concealed tooth cleaning implement. People use many devices to remove particles of food or other debris from between their teeth. Such devices include toothpicks, dental floss, small brushes, and metal scalers. With the exception of toothpicks, use of these devices is mostly confined to non-public locations. After dining or eating, food and other debris often becomes lodged in between a person's teeth. For example, because of table etiquette, it is difficult to dislodge the food in a polite manner at the table after a meal.

The present invention is a case that appears to be a lipstick application dispenser but with a dental scaler concealed in a faux lipstick tube. The device is designed to fool an observer into believing that the user is applying lipstick rather than picking at or removing food between teeth. It is thus an object of the present invention to conceal the use of a tooth cleaning device in a public location by using an apparatus containing a tooth cleaning implement disguised in a holder such as a lipstick holder or other similar holder.

The present invention is a disguised holder for supporting a concealed tooth cleaning implement having an elongated case having a handle portion and a base portion, the base portion supporting a tooth cleaning implement, an elongated flexible member supported by the base portion and concealing the tooth pick implement and the elongated member having an opening. The tooth cleaning implement is concealed within the flexible member. The flexible member is tubular in shape. The tooth cleaning implement and the flexible member are supported by a walled support integral with the base portion, a cap having a closed end and an open end for engagement with the walled support so that the closed end of the cap covers the flexible member when the open end of the cap is engaged with the walled support. The base portion of the case has a storage area for storing one or more of the tooth cleaning implements. The elongated case has a longitudinal axis and the tooth cleaning implement is a tooth scaler having a base portion, a shank portion generally parallel to the longitudinal axis of the case and a tip portion generally perpendicular to the longitudinal axis of the case. The tip portion of the scaler protrudes through the opening when the flexible member portion is deformed in the area of the opening. The elongated case has a longitudinal axis and the tooth cleaning implement can also be a tooth pick aligned along the longitudinal axis of the case.

The elongated case appears as a lipstick case and the flexible member appears as a tube of lipstick.

BRIEF DESCRIPTION OF THE DRAWINGS

FIG. 2 is a view of a holder for a concealed tooth cleaning implement indicating sections 7-7 and 6-6.

FIG. 3 is a top-down view of the holder for a concealed tooth cleaning implement.

FIG. 4 is a view of the holder for a concealed tooth cleaning implement with a removable cap.

FIG. 5 is a view of the holder for a concealed tooth cleaning implement showing the projection of the tip of the implement when a force F is applied to the faux lipstick.

FIG. 6 is a cross-section, 6-6, of the concealed scaler dispenser showing a storage compartment in the base with one or more replaceable scaler's in storage.

FIG. 7 is a cross-section, 7-7, of the concealed scaler dispenser.

DETAILED DESCRIPTION OF A PREFERRED EMBODIMENT

Figure 1:
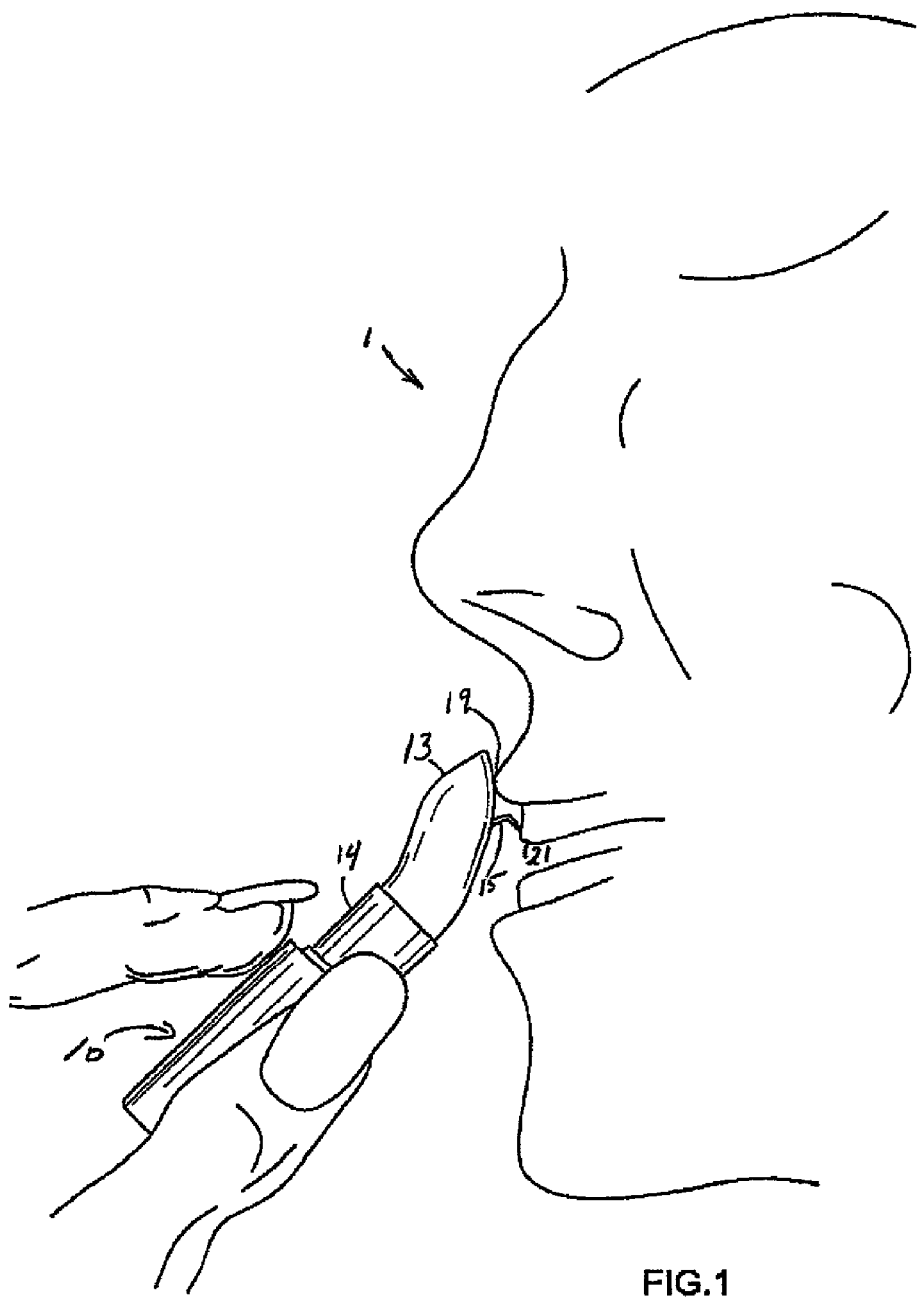
FIG. 1 demonstrates use of the concealed tooth cleaning implement on a user's teeth.
Figure 8:
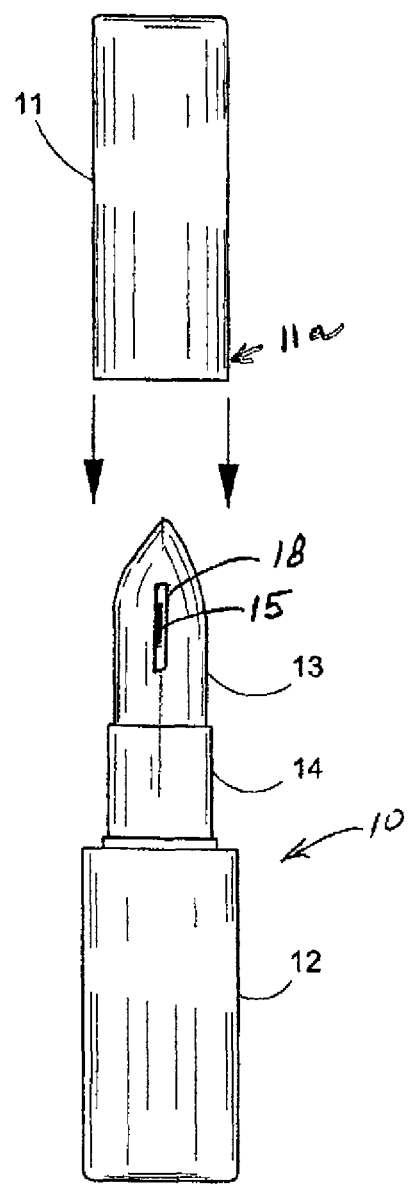
FIG. 8 is a partial front view of faux lipstick 13 showing opening 18 for scaler tip 15 to protrude.

A tooth cleaning implement, such as a scaler 15, is designed to remove particles of food or other debris from between teeth 21 of a person 1. Concealed or hidden within in a faux lipstick case 10 is the scaler 15. Case 10 has a handle portion 12 and a base portion 12a. Base portion 12a has an internally threaded inner bore 12b. The scaler 15 is positioned within a flexible tube that appears as faux lipstick 13. The faux lipstick 13 tube appears to look like a tube of lipstick within case 10 which appears to look like a lipstick case. The scaler 15 is securely positioned and held in the base portion 12a of the faux lipstick case 10 as shown in section 6-6 in FIG. 6 and section 7-7 of FIG. 7. A removable support holder 14 has a circumferential wall 14a that is externally threaded at its base 14b. Base 14b screws into base portion 12a. When fully tightened within base 12a, holder 14 supports and holds faux lipstick 13 and scaler 15 at base 12a of case 10. Base 12a has internal threading 12b to receive base 14b of holder 14. Further the bottom portion 14c of support holder 14 tightens down on flange 15b at the base of scaler 15 in order to hold scaler 15 in place within base portion 12a of case 10. Scaler 15 has a mid-portion or shank portion 15c.

Faux lipstick 13 has an opening near the top portion of faux lipstick 13. The tip 15a of scaler 15 protrudes through opening 18 within the flexible faux lipstick 13, as shown in FIG. 5, when a generally perpendicular force to the longitudinal axis of the flexible faux lipstick 13 is applied, such as by pressing the flexible faux lipstick 13 against a person's lip 19 or alternatively against a person's teeth 21. As shown in FIG. 1 once the tip 15a of scaler 15 is revealed, it can be positioned between the teeth 21 so any foreign food particles may be removed by movement of the scaler 15 against teeth 21, while it appears to an observer that the user, person 1, is merely applying the faux lipstick 13. When not in use, a cap 11 is positioned over the faux lipstick 13. Cap 11 is generally cylindrical having a closed top end and an open bottom end 11a. Cap 11 slides onto support wall 14a with a friction fit between the inner lower portion 11a of cap 11 and wall 14a. Cap 11 is removably mounted to the base portion 12a of faux lipstick case 10.

Additional disposable scalers 15 can be held in a storage compartment 16 in the handle portion 12 of the dispenser case 10 as shown in FIG. 6. Scalers 15 have a base flange 15b that support holder 14 screws down to hold scaler 15 in place in the inner base portion 12c of case 10.

Scaler 15 when being replaced can be removed and disposed of or stored in compartment 16 when a new scaler 15 is used. Access to the storage compartment 16 is through an internal bore 12c.

Scaler 15 protrudes through opening 18 in faux lipstick 13 when faux lipstick 13 is pressed against an object such as lip 19, the opening 18 remains closed when scaler 15 is not protruding there through. Opening 18 is shown at the top portion and at the side of faux lipstick 13, however if a different implement were used, the opening could be placed anywhere within the faux lipstick 13. For example if the implement were a toothpick, a straight implement, the opening would be at the top of faux lipstick 13.

Cap 11 is held in place on case 10 with an internal friction fit against the support holder 14. Thus support holder 14 holds cap 11 in place when it is attached to case 10. Support holder 14 also holds faux lipstick 13 in place and scaler 15 in place when it is screwed into base portion 12a. Support 14 is cylindrical and has threaded screws 14b at its base to secure support 14 against handle 12 at the base 12a of case 10. When fully screwed down, support 14 holds scaler 15 in place and puts pressure against flange 15b to hold scaler 15 in place and from rotating. Additionally faux lipstick 13 is held in place within the circumferential walls 14a of support 14 such that scaler 15 is within faux lipstick 13. Tip 15a of scaler 15 is perpendicular to the longitudinal axis of case 10. Opening 18 is aligned to allow tip 15a to protrude through opening 18 when faux lipstick 13 is deformed in the area of opening 18.

It is to be understood that the preceding is merely a detailed description of the invention, and that alterations to the disclosed invention can be made in accordance with the disclosure without departing from the spirit and scope of the invention. The preceding description is not meant to limit the scope of the invention. The scope of the invention is to be determined by the appended claims and their equivalents.

We claim:

1. A holder for supporting a concealed tooth cleaning implement comprising:
   a base portion;
   a tooth cleaning implement disposed on said base portion;
   a flexible member disposed on said base portion and concealing said tooth cleaning implement therein;
   said flexible member having an opening formed therein for allowing a tip portion of said tooth cleaning implement to protrude through said opening when said flexible member is deformed in an area of said opening.

2. The holder according to claim 1, further comprising a cap removably mounted on said base portion, said cap concealing said flexible member.

* * * * *